United States Patent
Von Oepen et al.

(10) Patent No.: US 6,497,722 B1
(45) Date of Patent: Dec. 24, 2002

(54) METHODS AND APPARATUS FOR IN-VIVO TAILORED STENTS INDICATED FOR USE IN TORTUOUS ANATOMY

(75) Inventors: Randolf Von Oepen, Hirrlingen (DE); Kenneth J. Michlitsch, Schaffhausen (CH)

(73) Assignee: Jomed GmbH, Rangendingen (DE)

( * ) Notice: Subject to any disclaimer, the term of this patent is extended or adjusted under 35 U.S.C. 154(b) by 0 days.

(21) Appl. No.: 09/718,589

(22) Filed: Nov. 22, 2000

Related U.S. Application Data

(63) Continuation-in-part of application No. 09/303,867, filed on May 3, 1999, now abandoned.

(30) Foreign Application Priority Data

May 4, 1998 (DE) .......................................... 198 19 629

(51) Int. Cl.$^7$ .................................................. A61F 2/06
(52) U.S. Cl. ...................................... 623/1.13; 623/1.2
(58) Field of Search ............................... 623/1.12, 1.13, 623/1.18, 1.2, 1.3, 1.31, 1.44, 1.11, 1.17, 1.21; 606/108, 190, 194, 198

(56) References Cited

U.S. PATENT DOCUMENTS

| | | | |
|---|---|---|---|
| 5,405,377 A | 4/1995 | Cragg | 623/1.2 |
| 5,645,559 A | 7/1997 | Hachtmann et al. | 623/1.2 |
| 5,665,115 A | 9/1997 | Cragg | |
| 5,683,448 A | 11/1997 | Cragg | 623/1.13 |
| 5,735,892 A | 4/1998 | Myers et al. | 623/1.13 |
| 5,766,237 A | 6/1998 | Cragg | |
| 5,788,626 A | 8/1998 | Thompson | 600/36 |
| 5,817,102 A | 10/1998 | Johnson et al. | 606/108 |
| 5,843,158 A * | 12/1998 | Lenker et al. | 623/11 |
| 5,876,448 A | 3/1999 | Thompson et al. | 623/1.13 |
| 6,010,530 A * | 1/2000 | Goicoechea | 623/1.13 |
| 6,017,363 A * | 1/2000 | Hojeibane | 623/1.35 |
| 6,086,610 A * | 7/2000 | Duerig et al. | 623/12 |
| 6,315,791 B1 * | 11/2001 | Gingras et al. | 623/1.46 |

* cited by examiner

Primary Examiner—Cary E. O'Connor
(74) Attorney, Agent, or Firm—Michael J. Striker

(57) ABSTRACT

Apparatus and methods for stenting are provided comprising a self-expandable stent that is at least partially covered with a biocompatible material configured to prevent dynamic self-expansion of the stent. The biocompatible material is irreversibly expandable by suitable means, for example, a balloon. Thus, the apparatus may be tailored in-vivo to a vessel profile, in a manner similar to a balloon-expandable stent, but maintains the flexibility required for use in tortuous anatomy and in vessels that undergo temporary deformation, in a manner similar to a self-expandable stent. Apparatus is also provided for stenting at a vessel branching, and for localized delivery of therapeutic agents.

37 Claims, 4 Drawing Sheets

METHODS AND APPARATUS FOR IN-VIVO TAILORED STENTS INDICATED FOR USE IN TORTUOUS ANATOMY

REFERENCE TO RELATED APPLICATIONS

This application is a continuation-in-part of U.S. patent application Ser. No. 09/303,867 filed May 3, 1999, now abandoned which claims priority from German Patent application 198 19 629.6 filed May 4, 1998.

FIELD OF THE INVENTION

The present invention relates to stents. More particularly, the present invention provides apparatus and methods for stenting that are indicated for use in tortuous anatomy and in vessels that undergo temporary deformation, and furthermore that may be tailored to an appropriate profile in-vivo.

BACKGROUND OF THE INVENTION

Stents are commonly indicated for a variety of intravascular applications, including restoration and/or maintenance of patency within a patient's vessel. They are also used to prevent restenosis of the blood vessel post-dilation, thereby ensuring adequate blood flow through the vessel. In certain applications, for example, in the carotid arteries, stents must further prevent release of embolic material from the walls of the vessel. Blood flow may carry such embolic material downstream into the vasculature of the patient's brain, where the material may occlude flow and cause stroke or other permanent damage to the patient.

Conventional stents are formed of a cell or mesh structure having interstitial spaces that limit the ability of such stents to prevent release of emboli. Thus, stent grafts often are used in order to seal stenotic emboli against the vessel wall. A stent graft comprises a stent, which is at least partially covered with a biocompatible material that is impermeable to stenotic emboli. In addition to preventing release of emboli, stent grafts are indicated for bridging defective points within a vessel, such as aneurysms, ruptures, dissections, punctures, etc.

The graft covering material may comprise a biocompatible polymer, such as Polyethylene Terephthalate (PET? or "Dacron") or Polytetrafluoroethylene (PTFE or "Teflon"), or, alternatively, the material may be homologic, for example, an autologous or non-autologous vein. PETP-covered stent grafts typically are only able to expand in the single dimension in which the fabric has been tensioned. Thus, the dimension of the vessel to be treated must be determined in advance, and potential for in-vivo diameter adjustment of PETP-covered grafts is limited.

Stent grafts may be either balloon-expandable or self-expandable. Advantageously, balloon-expandable systems may be expanded to an optimal diameter in-vivo that corresponds to the internal profile of the vessel. However, as compared to self-expandable stents, balloon-expandable stents are fabricated from relatively rigid materials, such as stainless steel. Balloon-expandable stents and stent grafts are therefore not indicated for use in tortuous anatomy or in vessels that may be temporarily deformed, for example, through contact with neighboring muscles, through joint motion, or through pressure applied externally to the patient.

Conversely, self-expandable stents and stent grafts characteristically return in a resilient fashion to their unstressed deployed configurations after being compressed and are thus indicated for use in tortuous anatomy and in vessels that undergo temporary deformation. Fabrication materials for self-expandable stents include superelastic materials, such as nickel-titanium alloys ("NITINOL"), spring steel, and polymeric materials. Alternatively, the stents may be fabricated from elastic materials comprising resilient knit or wickered weave patterns.

A drawback of self-expandable stents is that they have deployed diameters that cannot be adjusted in-vivo. Since it is difficult to accurately determine the internal diameter of a vessel, self-expandable stents are commonly implanted with deployed diameters that are too large or too small for a given application. It the selected stent diameter is too large, the stent applies a permanent pressure against the vessel wall, which over time may cause the vessel to expand and adjust to the geometry of the stent. This is highly undesirable, as it alters the natural flow characteristics of the vessel with unpredictable results. Alternatively, if the deployed diameter is too small, the stent may not tightly abut against the vessel wall. Turbulent flow may develop in the gap between the vessel wall and the stent, thereby leading to dangerous thrombus formation, or the stent may dislodge and flow downstream with potentially fatal consequences. Further still, the diameter of a vessel may change along its length, in which case selection of a properly dimensioned self-expandable stent is essentially not possible.

When used in a stent graft, self-expandable stents are typically covered with a biocompatible material that is dimensioned to correspond to either the expanded deployed, or the collapsed delivery configuration of the stent. When dimensioned for the deployed configuration, the stent is collapsed to the delivery configuration, and the biocompatible material is folded onto and bonded to the stent such that the material becomes taut only when the stent dynamically expands to the deployed configuration. When dimensioned for the delivery configuration, the material has sufficient elasticity to expand with the stent without limiting or preventing self-expansion of the stent. In either case, the stent dynamically expands to its fully deployed configuration, providing a medical practitioner with no opportunity to tailor the stent in-vivo to the patient's unique anatomy.

In view of the drawbacks associated with previously known stents and stent grafts, it would be desirable to provide apparatus and methods for stenting that overcome these drawbacks.

It also would be desirable to provide apparatus and methods for stenting that allow in-vivo tailoring of stent diameter.

It further would be desirable to provide apparatus and methods for stenting that are indicated for use in tortuous anatomy and in vessels that undergo temporary deformation.

It would be desirable to provide apparatus and methods for stenting that are indicated for use at a vessel branching.

SUMMARY OF THE INVENTION

In view of the foregoing, it is an object of this invention to provide apparatus and methods for stenting that overcome the drawbacks of previously known apparatus and methods.

It is another object of this invention to provide apparatus and methods that allow in-vivo tailoring of stent diameter.

It is yet another object of the present invention to provide apparatus and methods for stenting that are indicated for use in tortuous anatomy and in vessels that undergo temporary deformation.

It is an object of the present invention to provide apparatus and methods for stenting that are indicated for use at a vessel branching.

These and other objects of the present invention are accomplished by providing apparatus for stenting comprising a self-expandable stent that is at least partially covered with a biocompatible material configured to prevent dynamic self-expansion of the stent. The biocompatible material is irreversibly expandable by suitable means, for example, by a balloon or other inflatable member, but has sufficient tensile strength and is attached to the stent in such a manner that hoop stress applied by the stent in the delivery configuration is not sufficient to achieve irreversible expansion of the material. Thus, the present invention provides apparatus that may be tailored in-vivo to a vessel profile, in a manner similar to a balloon-expandable stent or stent graft, but that maintains required flexibility for use in tortuous anatomy and in vessels that undergo temporary deformation, in a manner similar to a self-expandable stent or stent graft.

In a first embodiment, the biocompatible material preferably comprises a high-strength PTFE fabric or a homologic material that is wrapped around and tautly attached to the stent in a collapsed delivery configuration. The material is preferably impermeable to stenotic emboli. Additionally, the material may comprise a coating configured for localized delivery of therapeutic agents or for inhibition of thrombus formation.

The stent preferably comprises a superelastic material, such as a nickel titanium alloy, spring steel, or a polymeric material. Alternatively, the stent may be fabricated with a resilient knit or wickered weave pattern of elastic materials, such as stainless steel. At least a portion of the stent is preferably radiopaque to facilitate proper positioning of apparatus of the present invention within a vessel.

The apparatus is mounted on a balloon catheter in the delivery configuration for delivery to a treatment site. Upon delivery using well-known techniques, the balloon catheter is inflated with sufficient pressure to facilitate irreversible expansion of the biocompatible material and to anchor the apparatus against the vessel wall with an in-vivo tailored diameter. A plurality or balloons having different diameters may be used to further tailor the stent diameter to the profile of the vessel. Stent diameter may even be varied along the length of stenting by inserting a balloon only partially inside the stent during inflation, or by using balloons of lengths shorter than the length of the stent. Importantly, and in contrast to conventional balloon-expandable systems, embodiments of the present invention characteristically deform and return in a resilient fashion to their tailored configurations after being compressed or deformed by an outside force.

In an alternative embodiment, apparatus is provided for use at a vessel branching, wherein the stent and biocompatible material comprise a radial opening. When stenting at the vessel branching, the opening may be positioned in line with the side branch to maintain patency of the branch. Furthermore, a plurality of radial openings may be provided along the length of the implant as required to ensure continuous blood flow through a plurality of side branches.

Methods of using the apparatus of the present invention are also provided.

BRIEF DESCRIPTION OF THE DRAWINGS

Further features of the invention, its nature and various advantages will be more apparent from the following detailed description of the preferred embodiments, taken in conjunction with the accompanying drawings, in which like reference numerals apply to like parts throughout, and in which.

DETAILED DESCRIPTION OF THE INVENTION

The present invention provides apparatus and methods for stenting that are indicated for use in tortuous anatomy and in vessels that undergo temporary deformation, and that may be tailored to an appropriate profile in-vivo. Unlike previously known stents and stent grafts, the present invention provides the tailor-ability of balloon-expandable systems with the resiliency of self-expandable systems.

Figure 1A:
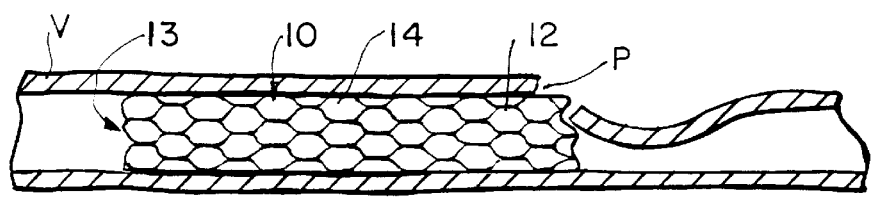
FIGS. 1A and 1B are side-sectional views of a prior art balloon-expandable stent graft in an expanded deployed configuration within a patient's vasculature, illustrating, respectively, the inability of balloon-expandable grafts to undergo temporary deformation and to be implanted in tortuous anatomy.
Figure 1B:
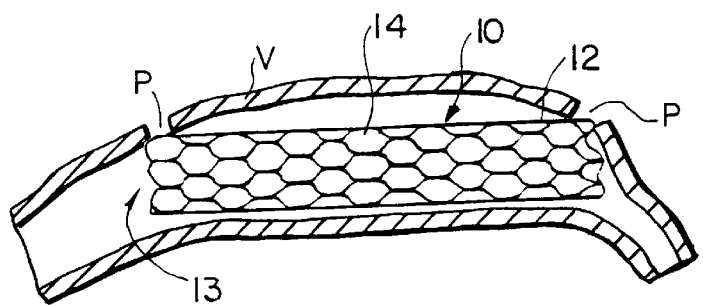

Referring to FIGS. 1A and 1B, the limitations of a prior art, balloon-expandable stent graft are discussed in greater detail. In FIG. 1A, balloon-expandable stent graft 10 is shown within a patient's vessel V that is undergoing temporary deformation, for example, due to contact with neighboring muscles, through joint motion, through pressure applied externally to the patient, etc. Stent graft 10 comprises balloon-expandable stent 12 having lumen 13. Stent 12 is fabricated from a suitably rigid material, such as stainless steel. Stent 12 is covered with biocompatible material 14, which commonly comprises PTFE, PETP, or a homologic material.

As illustrated in FIG. 1A, while the diameter of stent 12 may be tailored in-vivo to the profile of vessel V using balloon expansion, the rigidity of stent 12 limits its ability to track curvature within the vessel or deform. Thus, stent graft 10 may dissect vessel V at puncture site P during temporary deformation of the vessel. Alternatively, temporary deformation of vessel V may cause plastic deformation of graft 10 that reduces lumen 13 and prevents vessel V from resuming its non-deformed profile (not shown). Clearly, either of these conditions creates a serious risk to the life of the patient; balloon-expandable stents and stent grafts are therefore contraindicated for use in vessels that undergo temporary deformation.

With reference to FIG. 1B, stent graft 10 is shown in the expanded deployed configuration within a patient's vessel V exhibiting tortuous anatomy. As with the temporary deformation of FIG. 1A, stent 12 lacks the necessary flexibility to conform to the tortuous profile of vessel V and may again puncture the vessel at puncture site P, or may force the vessel to assume the profile of stent 12 (not shown). Thus, balloon expandable stents and stent grafts are also contraindicated for use in tortuous anatomy.

Figure 2A:
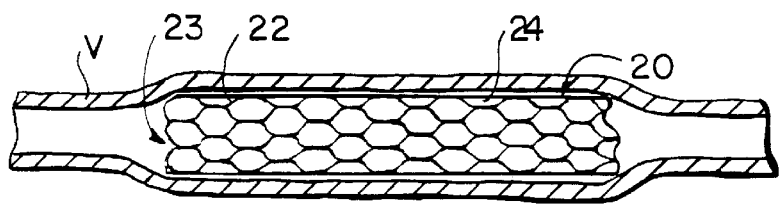
FIGS. 2A and 2B are side-sectional views of a prior art self-expandable stent graft in an expanded deployed configuration within the patient's vasculature, illustrating, respectively, a self-expandable graft having a diameter that is too large and too small.
Figure 2B:
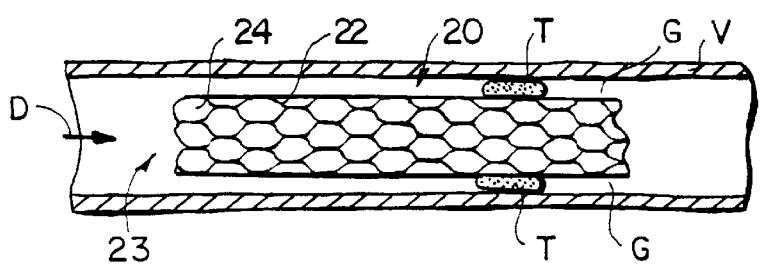

Referring now to FIGS. 2A and 2B, the limitations of a prior art, self-expandable stent graft are discussed in greater detail. In FIG. 2A, stent graft 20 has a larger deployed diameter than the internal diameter of vessel V. Stent graft 20 comprises self-expandable stent 22, having lumen 23. Stent 22 is fabricated from a suitably resilient material, such as spring steel or NITINOL. Stent 22 is covered with biocompatible material 24, which does not inhibit or prevent dynamic expansion of stent 22 to the deployed configuration of FIGS. 2.

As illustrated in FIG. 2A, while the flexibility and resiliency of self-expandable stent 22 indicate the stent for use in tortuous anatomy and in vessels that undergo temporary deformation, the stent cannot be tailored in-vivo to the profile of vessel V. Thus, if a self-expandable stent of improper deployed diameter is implanted within the vessel, serious risks to the life of the patient arise. In FIG. 2A, since stent 22 has a deployed diameter that is larger than the internal diameter of vessel V, stent graft 20 applies a constant pressure against the wall of vessel V. Over time, vessel V may expand and adjust to the geometry of stent graft 20. This is highly undesirable, as it alters natural flow characteristics within the vessel in unpredictable ways.

In FIG. 28, stent graft 20 has a deployed diameter that is smaller than the internal diameter of vessel V, and thus does not tightly abut against the vessel wall. Blood flowing through vessel V in direction D may exhibit turbulent flow in gap G between graft 20 and vessel V. This may, in turn, lead to potentially fatal thrombus formation T. Alternatively, the blood flow may carry stent graft 20 downstream, where it may lodge against smaller vasculature and occlude flow (not shown).

Figure 3A:
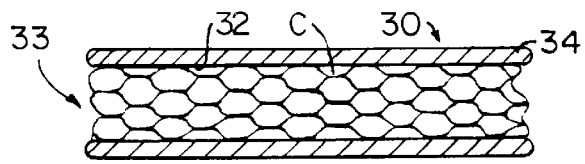
FIGS. 3A–3C are side-sectional views of apparatus of the present invention, shown, respectively, in a collapsed delivery configuration, partially positioned over a balloon catheter, and in a tailored deployed configuration.
Figure 3B:
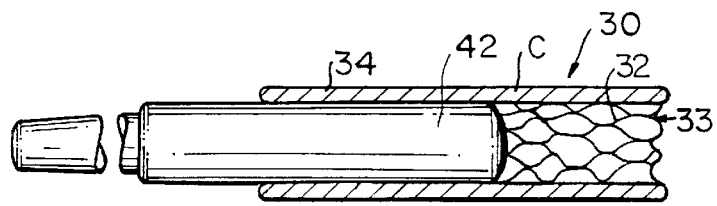
Figure 3C:
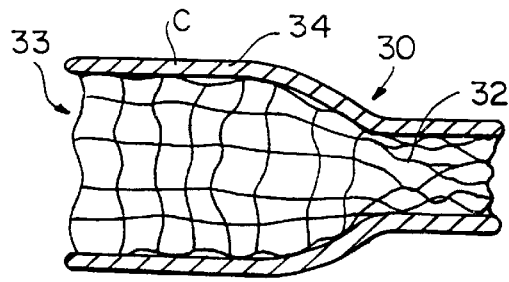

The present invention combines the beneficial aspects of balloon-expandable systems with the beneficial aspects of self-expandable systems, while removing significant drawbacks of both systems. Referring to FIGS. 3A–3C, a first embodiment of apparatus of the present invention is described. As seen in FIG. 3A, apparatus 30 comprises self-expandable stent 32 having lumen 33, and biocompatible material 34 that at least partially covers stent 32. Biocompatible material 34 prevents dynamic self-expansion of stent 32. In the context of the present invention, material 34 at least partially covering stent 32 includes, but is not limited to, material 34 at least partially covering an internal or an external surface of stent 32, material 34 being sintered within apertures of stent 32, and combinations thereof.

Material 34 is irreversibly expandable by suitable means, for example, by a balloon or other inflatable member, but has sufficient tensile strength along the direction of loading, and is attached to stent 32 in such a manner, that hoop stress applied by stent 32 in the delivery configuration of FIG. 3A is not sufficient to achieve irreversible expansion of the material. Thus, apparatus 30 may be tailored in-vivo to a patient's vessel profile, in a manner similar to a balloon-expandable system, while maintaining required flexibility and resiliency for use in tortuous anatomy and in vessels that undergo temporary deformation, in a manner similar to a self-expandable system.

Stent 32 preferably comprises a superelastic material, such as a nickel titanium alloy, spring steel, or spring steel. Alternatively, stent 32 may be fabricated with a resilient knit or wickered weave pattern of conventional elastic materials, such as stainless steel. At least a portion of stent 32 is preferably radiopaque to facilitate positioning of apparatus 30 within a patient's vessel.

Biocompatible material 34 preferably comprises a high-strength PTFE fabric or a homologic material that is wrapped around and tautly attached to stent 32, while stent 32 is held in the delivery configuration. Material 34 exhibits sufficient tensile strength in the radial direction of expansion of stent 22 to prevent self-expansion of the stent. Material 34 is preferably impermeable to stenotic emboli. Material 34 may further comprise optional coating C that locally releases drugs, gene vectors, or other therapeutic agents when implanted in a vessel. Coating C may alternatively comprise a substance that inhibits thrombus formation, for example, Heparin.

As seen in FIG. 3B, with apparatus 30 in the collapsed delivery configuration, balloon 42 of balloon catheter 40 is inserted at least partially within lumen 33 of stent 32, and apparatus 30 is delivered to a treatment site. Balloon 40 is then inflated with sufficient pressure to facilitate irreversible expansion of biocompatible material 34, as seen in FIG. 3C.

Since the diameter of a vessel may differ over the length of stenting by two or more millimeters, for example, at the transition from the common carotid artery to the internal or external carotid, in-vivo tailoring of stent diameter along the length of the stent is highly desirable. As is clear from FIG. 3C, by controlling the insertion depth of balloon catheter 40 within lumen 33 of apparatus 30, and by controlling the degree of inflation of balloon 42, an implant having a diameter tailored in-vivo to the profile of a treatment site may be achieved. Apparatus 30 may further be tailored along its length by using a plurality of balloon catheters having balloons of different diameters and/or lengths. Additionally, balloon 42 may be provided with a non-uniform expanded profile that apparatus 30 mirrors upon expansion. Importantly, and in contrast to conventional balloon-expandable systems, apparatus 30 of the present invention is indicated for use in tortuous anatomy and in vessels that undergo temporary deformation. Apparatus 30 characteristically deforms and returns in a resilient fashion to its tailored deployed configuration after being compressed or deformed by an outside force.

Figure 4A:
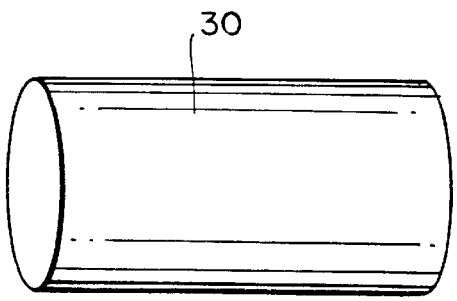
FIGS. 4A–4C are side views of the apparatus of FIG. 3A in alternative tailored deployed configurations.
Figure 4B:
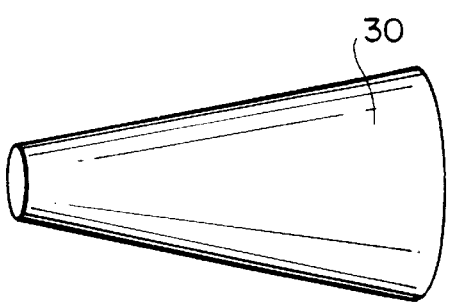
Figure 4C:
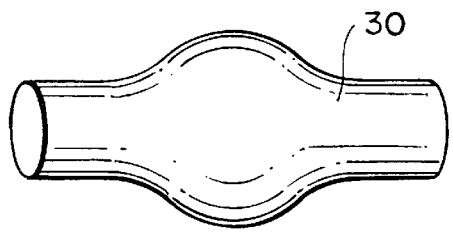

Referring now to FIGS. 4A–4C, illustrative examples of alternative deployed configurations of the apparatus of FIG. 3A, tailored to chosen profiles, are provided. In FIG. 4A, apparatus 30 has been expanded to the deployed configuration evenly along its length, providing an implant with a constant diameter. In FIG. 4B, apparatus 30 has been expanded with a tapered profile, as may, for example, be accomplished by inflating a plurality of balloons of progressively larger diameter inserted to progressively shallower depths within lumen 33 of apparatus 30, or by inflating a balloon with a tapered expanded profile. In FIG. 4C, apparatus 30 has been expanded to the deployed configuration with a central bulge, as may, for example, be accomplished with a balloon of length shorter than the length of apparatus 30 that is positioned within the central region of apparatus 30 and inflated. As will, of course, be apparent to those of skill in the art, apparatus 30 may be tailored to a wide variety of additional profiles in accordance with the present invention.

Figure 5A:
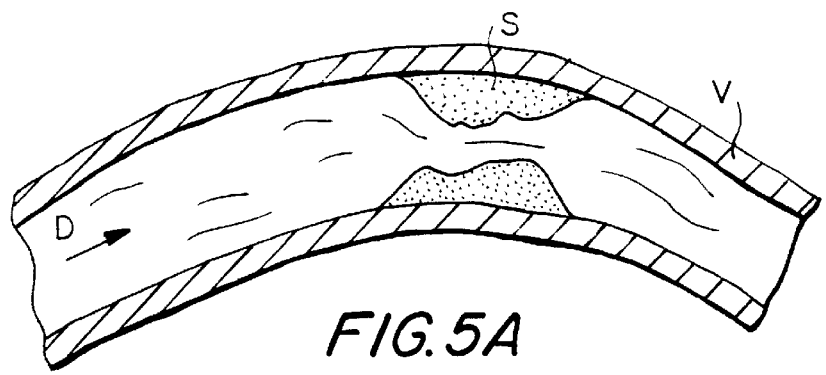
FIGS. 5A–5D are side-sectional views of the apparatus of FIGS. 3 within a patient's vasculature, illustrating a method of using the apparatus in accordance with the present invention.
Figure 5B:
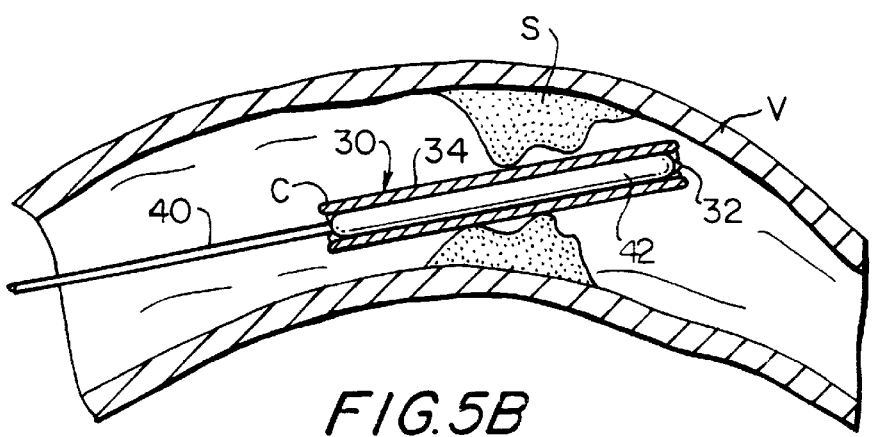

With reference to FIGS. 5A–5D, a method of using the apparatus of FIGS. 3 within a patient's vasculature to provide an implant tailored in-vivo is described. In FIG. 5A, vessel V, exhibiting tortuous anatomy, is partially occluded with stenosis S that disrupts blood flow in direction D. Using well-known techniques, apparatus 30, disposed in the collapsed delivery configuration over balloon 42 of balloon catheter 40, is advanced to the point of stenosis, as seen in FIG. 5B. Radiopacity of stent 32, viewed under a fluoroscope, may facilitate proper positioning of apparatus 30 within the vessel.

Figure 5C:
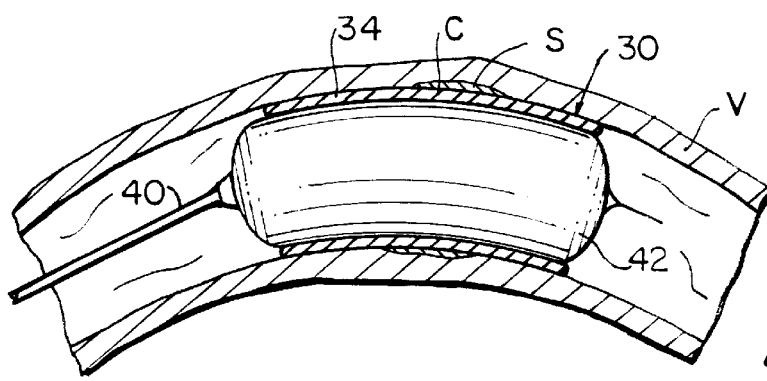

Biocompatible material 34 prevents dynamic self-expansion of self-expandable stent 32 of apparatus 30. In FIG. 5C, balloon 42 is inflated to irreversibly expand material 34 until apparatus 30 is anchored to the vessel wall and closely tracks the internal profile of vessel V. The deployed diameter of apparatus 30 is tailored in-vivo to the internal diameter of vessel V by adjusting the level of inflation of balloon 42, as well as by pre-selecting the fully inflated diameter of the balloon. Conventional self-expandable stent grafts do not provide this tailor-ability, as discussed previously.

Figure 5D:
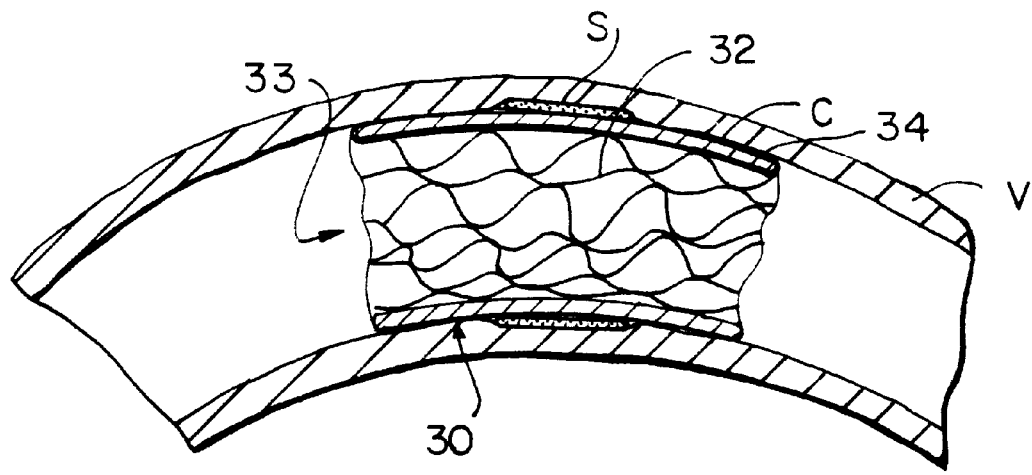

As seen in FIG. 5D, balloon 42 is then deflated, and balloon catheter 40 is removed from the vessel. Apparatus 30 assumes the tortuosity of vessel V due to the flexibility of self-expandable stent 32 of apparatus 30. Conventional balloon-expandable stents are not able to track such tortuosity, as discussed previously. Optional coating C on material 34 may then deliver drugs, gene vectors, thrombus inhibitors, or other therapeutic substances to the vessel wall, or directly into the blood stream. If, after a period of time, vessel V expands or exhibits restenosis at the treatment site, an additional balloon catheter may be introduced into lumen 33 of apparatus 30 and inflated to ensure that apparatus 30 maintains a deployed configuration tailored to the vessel profile (not shown).

Apparatus 30 compresses and seals stenosis S against the wall of vessel V, thereby preventing embolic material from the stenosis from traveling downstream. Alternatively, via angioplasty or other suitable means, stenosis S may be compressed against the vessel wall prior to insertion of apparatus 30. In addition to the application of FIGS. 5, apparatus 30 may be used for a variety of other applications, including, but not limited to, bridging defective points within a vessel, such as aneurysms, ruptures, dissections, punctures, etc. While FIGS. 5 depict vessel V with a relatively constant internal diameter, this is only for purposes of illustration, and it should be understood that apparatus 30 also may be tailored to fit more complicated vessel geometries, as illustrated hereinbelow.

Figure 6:
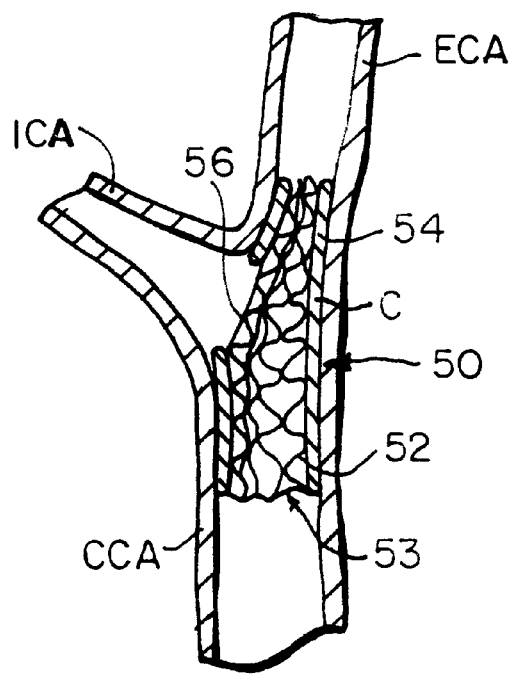
FIG. 6 is a side-sectional view of an alternative embodiment of the apparatus of the present invention in use at a vessel branching.

Referring now to FIG. 6, an alternative embodiment of the present invention is shown in use at a vessel branching. Apparatus 50 is similar to apparatus 30 of FIGS. 3–5, except that the apparatus comprises a radial opening to allow unimpeded blood flow to a vessel side branch at the point of stenting. Apparatus 50 comprises self-expandable stent 52 having lumen 53. Preferably, at least a portion of stent 52 is radiopaque. Biocompatible material 54 covers stent 52. The material preferably is impermeable to stenotic emboli and optionally may comprise coating C for delivery of therapeutic agents or thrombus inhibitors. Material 54 prevents dynamic self-expansion of stent 52. Radial opening 56 extends through stent 52 and material 54, thereby providing a side path for blood flow into and through lumen 53.

In FIG. 6, apparatus 50 has been expanded to a tailored deployed configuration within common carotid artery CCA and external carotid artery ECA. The external carotid has a smaller diameter than the common carotid, and, using techniques discussed previously, apparatus 50 has been tailored in-vivo to closely track this diameter change. Furthermore, if an angle were to exist between the CCA and the ECA, or if the carotids were to undergo temporary deformation, apparatus 50 would dynamically adjust to the anatomical constraints due to the use of self-expandable stent 52. Prior to expansion of apparatus 50, radial opening 56 was aligned with internal carotid artery ICA to ensure uninterrupted and unimpeded blood flow through the side branch The radiopacity of stent 52 may facilitate such alignment of opening 56 with a side branch. Additional embodiments of the present invention may be provided with a plurality of radial openings configured for use in vessels exhibiting a plurality of branchings.

While preferred illustrative embodiments of the present invention are described hereinabove, it will be apparent to those of skill in the art that various changes and modifications may be made therein without departing from the invention. For example, apparatus of the present invention may be expanded by suitable means other than a balloon or inflatable member. The appended claims are intended to cover all such changes and modifications that fall within the true spirit and scope of the invention.

What is claimed is:

1. Apparatus for stenting comprising:
   a self-expandable stent having proximal and distal ends, and a lumen extending therebetween, the stent having a collapsed deliver configuration and an expanded deployed configuration; and
   an irreversibly-expandable material covering at least a portion of the stent between the proximal and distal ends, the irreversibly-expandable material configured to prevent dynamic self-expansion of the stent from the delivery configuration to the deployed configuration,
   wherein the apparatus is adapted for percutaneous delivery to a treatment site without external constraint.

2. The apparatus of claim 1, wherein the self-expandable stent comprises a superelastic material.

3. The apparatus of claim 2, wherein the superelastic material is chosen from the group consisting of nickel titanium alloys, spring steel, and polymeric materials.

4. The apparatus of claim 1, wherein the self-expandable stent comprises a resilient weave pattern.

5. The apparatus of claim 1, wherein the irreversibly-expandable material comprises a biocompatible material.

6. The apparatus of claim 5, wherein the biocompatible material is chosen from the group consisting of biocompatible polymers, Polyethylene Terephthalate, Polytetrafluoroethylene, homologic materials, autologous veins, and non-autologous veins.

7. The apparatus of claim 1, further comprising a delivery catheter having an inflatable member configured to expand the irreversibly-expandable material, at least a portion of the self-expandable stent being disposed over the inflatable member in the collapsed delivery configuration,
   wherein the apparatus is adapted for percutaneous delivery to the treatment site without external constraint while disposed over the delivery catheter.

8. The apparatus of claim 7, wherein the inflatable member is configured to expand the stent and irreversibly-expandable material to a tailored deployed configuration.

9. The apparatus of claim 8, wherein the inflatable member is configured to expand the stent and irreversibly-expandable material to the tailored deployed configuration in-vivo.

10. The apparatus of claim 8, wherein the stent and material comprise flexibility in the tailored deployed configuration.

11. The apparatus of claim 8, wherein the tailored deployed configuration is configured to conform to an internal profile of a patient's vessel at a treatment site.

12. The apparatus of claim 7, wherein the inflatable member has an external profile that varies along a length of the inflatable member.

13. The apparatus of claim 7, further comprising a plurality of inflatable members, each of the plurality of inflatable members configured to expand the irreversibly-expandable material.

14. The apparatus of claim 1, wherein the apparatus is configured for use in tortuous anatomy.

15. The apparatus of claim 1, wherein the apparatus is configured for use in vessels that undergo temporary deformation.

16. The apparatus of claim 1, wherein the stent comprises flexibility in the expanded deployed configuration.

17. The apparatus of claim 1, wherein the stent is radiopaque.

18. The apparatus of claim 1, wherein the apparatus comprises at least one radial opening.

19. The apparatus of claim 18, wherein the at least one radial opening is configured for positioning at a vessel side branch to ensure blood flow through the side branch.

20. The apparatus of claim 1 further comprising a coating in communication with the irreversibly-expandable material.

21. The apparatus of claim 20, wherein the coating comprises a therapeutic agent configured for release when introduced into a blood vessel.

22. The apparatus of claim 21, wherein the therapeutic agent is chosen from the group consisting of drugs, gene vectors, and thrombus inhibitors.

23. The apparatus of claim 1, wherein the irreversibly-expandable material comprises an emboli-impermeable material.

24. A method for stenting, the method comprising:
providing apparatus comprising a self-expandable stent having proximal and distal ends, a lumen extending therebetween, and an irreversibly-expandable material covering at least a portion of the stent between the proximal and distal ends, the irreversibly-expandable material configured to prevent dynamic self-expansion of the stent from a collapsed delivery configuration to an expanded deployed configuration;
positioning at least a portion of the apparatus over an inflatable member;
advancing the apparatus to a treatment site within a patient's vessel without externally constraining the apparatus; and
inflating the inflatable member to expand the irreversibly-expandable material.

25. The method of claim 24, wherein inflating the inflatable member further comprises providing the apparatus with a tailored deployed configuration in which the apparatus contacts a wall of the patient's vessel at the treatment site.

26. The method of claim 25, further comprising inflating additional inflatable members within the lumen of the stent to provide the apparatus with the tailored deployed configuration.

27. The method of claim 25, wherein providing the apparatus with a tailored deployed configuration in which the apparatus contacts the wall of the patient's vessel at the treatment site further comprises sealing emboli against the wall.

28. The method of claim 25, further comprising
deflating and removing the inflatable member;
positioning a second inflatable member within the lumen of the self-expandable stent when an internal profile of the patient's vessel at the treatment site changes; and
inflating the second inflatable member to provide the apparatus with a newly tailored deployed configuration.

29. The method of claim 24, wherein advancing the apparatus to a treatment site comprises advancing the apparatus to a treatment site within the patient's vessel that is expected to undergo temporary deformation.

30. The method of claim 24, wherein advancing the apparatus to a treatment site comprises advancing the apparatus to a treatment site within the patient's vessel that exhibits tortuosity.

31. The method of claim 24, wherein providing apparatus further comprises providing apparatus having a radial opening through the stent and the material.

32. The method of claim 31, wherein advancing the apparatus to a treatment site comprises aligning the radial opening with a side branch of the patient's vessel.

33. The method of claim 24, wherein providing apparatus further comprises providing apparatus having a coating comprising therapeutic agents.

34. The method of claim 33, further comprising releasing the therapeutic agents from the coating into the patient's vessel.

35. The method of claim 24, wherein providing apparatus comprising a self-expandable stent further comprises providing apparatus comprising a radiopaque self-expandable stent.

36. The method of claim 35, wherein advancing the apparatus to a treatment site comprises facilitating proper positioning of the apparatus by imaging the radiopaque stent.

37. A method for stenting, the method comprising:
providing apparatus comprising a self-expandable stent having proximal and distal ends, a lumen extending therebetween, and an irreversibly-expandable material covering at least a portion of the stent between the proximal and distal ends, the irreversibly-expandable material configured to prevent dynamic self-expansion of the stent from a collapsed delivery configuration to an expanded deployed configuration;
positioning at least a portion of the apparatus over an inflatable member;
advancing the apparatus to a treatment site within a patient's vessel;
inflating the inflatable member to expand the irreversibly-expandable material and provide the apparatus with a tailored deployed configuration;
deflating and removing the inflatable member;
positioning a second inflatable member within the lumen of the self-expandable stent when an internal profile of the patient's vessel at the treatment site changes; and
inflating the second inflatable member to provide the apparatus with a newly tailored deployed configuration.

* * * * *